United States Patent
Chen et al.

(10) Patent No.: US 10,638,784 B2
(45) Date of Patent: May 5, 2020

(54) LACTOBACILLUS COMPOSITION FOR INHIBITING GASTRITIS INDUCED BY GASTRIC HELICOBACTER PYLORI AND USE THEREOF

(71) Applicant: GenMont Biotech Incorporation, Tainan (TW)

(72) Inventors: Yi-Hsing Chen, Tainin (TW); Wan-Hua Tsai, Kaohsiung (TW); Ya-Hui Chen, Chiayi County (TW); Chih-Ho Lai, New Taipei (TW); Yu-Hsin Lin, Taichung (TW)

(73) Assignee: GENMONT BIOTECH INCORPORATION, Tainan (TW)

(*) Notice: Subject to any disclaimer, the term of this patent is extended or adjusted under 35 U.S.C. 154(b) by 0 days.

(21) Appl. No.: 16/129,029

(22) Filed: Sep. 12, 2018

(65) Prior Publication Data
US 2020/0077692 A1    Mar. 12, 2020

(51) Int. Cl.
| | |
|---|---|
| A23L 33/14 | (2016.01) |
| A61K 35/747 | (2015.01) |
| A61P 1/04 | (2006.01) |
| A23L 33/135 | (2016.01) |

(52) U.S. Cl.
CPC .............. *A23L 33/135* (2016.08); *A23L 33/14* (2016.08); *A61K 35/747* (2013.01); *A61P 1/04* (2018.01); *A23Y 2220/03* (2013.01); *A23Y 2220/67* (2013.01); *A23Y 2220/73* (2013.01); *A23Y 2300/00* (2013.01)

(58) Field of Classification Search
None
See application file for complete search history.

(56) References Cited

U.S. PATENT DOCUMENTS

| | | | |
|---|---|---|---|
| 7,001,756 B1* | 2/2006 | Hsu | A61K 35/747 424/184.1 |
| 2005/0186189 A1* | 8/2005 | Hsu | A61K 35/747 424/93.45 |

OTHER PUBLICATIONS

Chen et al J Clin Med. Jan. 2019; 8(1): 90. (Year: 2019).*
Presti et al;Appl. Microbiol. Biotech. 2015;99:5613-5626 (Year: 2015).*
Turkova et al; Folia Microbiol. 2013;58:261-267 (Year: 2013).*
Lievin-Le Moal et al ;Clin. Microbiol. Rev. 2014;27:167-199 (Year: 2014).*
Delgado et al ; Front. Microbiol., Jan. 14, 2015 (Year: 2015).*

* cited by examiner

*Primary Examiner* — Padmavathi Baskar
(74) *Attorney, Agent, or Firm* — WPAT, PC

(57) ABSTRACT

The present invention provides a pharmaceutical composition and a food product for inhibiting gastritis induced by gastric *Helicobacter pylori*, comprising *Lactobacillus* selected from a group composed of *Lactobacillus rhamnosus* GM-020 (also known as GMNL-74) with deposited number CCTCC M203098; *Lactobacillus acidophilus* GMNL-185 with deposited number CCTCC M2017764; and *Lactobacillus plantarum* GMNL-662 with deposited number CCTCC M2016571; and any two of the above bacteria.

8 Claims, 4 Drawing Sheets

| adhesion activity of Lactobacillus strains on AGS | N (%) |
|---|---|
| - | 49 (22%) |
| + | 41 (18%) |
| ++ | 77 (34%) |
| +++ | 42 (18%) |
| ++++ | 18 (8 %) |
| Total | 226 (100%) |

F.

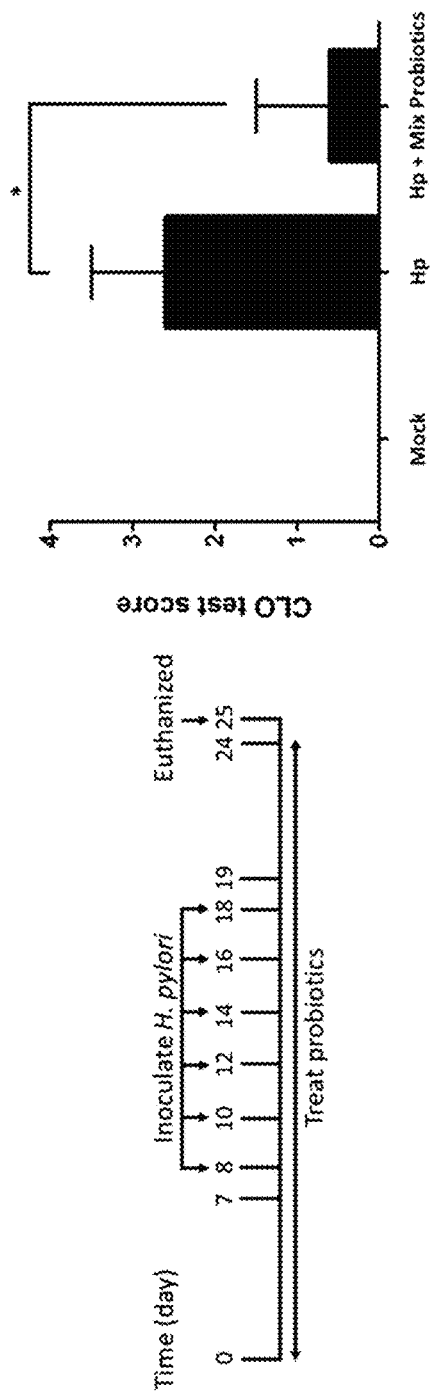
FIG. 4A
FIG. 4B
FIG. 4C

LACTOBACILLUS COMPOSITION FOR INHIBITING GASTRITIS INDUCED BY GASTRIC HELICOBACTER PYLORI AND USE THEREOF

BACKGROUND OF THE INVENTION

Field of the Invention

The present invention relates to the field of health care foods and more particularly to the use of a *Lactobacillus* composition for inhibiting gastritis induced by gastric *Helicobacter pylori*.

Description of the Related Art

*Helicobacter pylori* (*H. pylori*) is a microaerophilic Gram-negative bacterium that may cause gastrointestinal associated diseases including: gastric ulcer, duodenal ulcer, chronic gastritis, gastric mucosa-associated lymphoid tissue lymphoma and even gastric adenocarcinoma. *Helicobacter pylori* mainly uses its urease to decompose urea to produce ammonia and carbon dioxide ($CO_2$). Ammonia reacts with water to produce alkaline ammonium ions ($NH4^+$) to neutralize gastric acid and increase the pH of the mucosa up to 4.5-7.0, allowing the bacteria to survive in the gastric environment for a long period of time (Eaton K A, Suerbaum S, Josenhans C and Krakowka S. 1996). In addition, *Helicobacter pylori* secretes vacuolating cytotoxin A (VacA), the cytotoxin will increase the cell permeability, causing cell burst and inducing inflammatory response (Atherton J C, Peek R M, Jr., Than K T, Cover T L And Blaser M J 0.1997).

Another important toxin is cytotoxin-associated gene A (CagA). Studies have proved that CagA can activate the nuclear transcription factor kB (NF-κB) to activate the expression of downstream inflammation-associated cytokines; and it can promote the secretion of cytokine interleukine-8 (IL-8) to chemotaxis the aggregation of neutrophils, consequently makes the gastric epithelium to produce downstream inflammatory response (Backert S, Schwarz T, Miehlke S, Kirsch C, Sommer C, et al. 2004, Censini S, Lange C, Xiang Z, Crabtree J E, Ghiara P, et al. 1996), and causes gastrointestinal tract diseases after infected with *Helicobacter pylori*.

Currently, the therapy for *Helicobacter pylori* infection is usually to combine the following drugs for administration at the same time: (1) antibiotics, such as: amoxicillin, clarithromycin, metronidazole, etc.; (2) bismuth; and (3) acid inhibitor or proton pump inhibitor. However, *Helicobacter pylori* can easily produce resistance against antibiotics, and therefore, drugs are currently administrated by using triple or quadruple therapy with two types of antibiotics plus bismuth or proton pump inhibitor.

The main and obvious side effects of these drugs are parageusia, nausea, diarrhea, flatulence, encephalalgia and dizziness. If the patient stops taking the drugs voluntarily, it is easier to cause *Helicobacter pylori* to produce resistance to antibiotics. In general, about 10-20% of patients cannot eradicate the *Helicobacter pylori* infection because of the above reason. Therefore, it is desired for improvement in the existing therapies for the *Helicobacter pylori* infection.

Probiotics are microorganisms that have been proven through studies to be beneficial to human health; among them, the most widely used are *Lactobacillus* spp. and *Bifidobacterium* spp. In the adjuvant therapy for *Helicobacter pylori* infection, it has been discovered in recent years that the use of specific lactic acid bacteria strains can increase the clearance rate of antibiotic therapy for *Helicobacter pylori*, especially when the effect of the triple therapy is poor (Dang Y, Reinhardt J D, Zhou X and Zhang G. 2014). In addition, studies have shown that the use of lactic acid bacteria can also reduce the side effects caused by antibiotic therapy, including nausea, gastrointestinal discomfort and emesis (Gong Y, Li Y and Sun Q. 2015, Zhang M M, Qian W, Qin Y Y, He J and Zhou Y H. 2015, Lv Z, Wang B, Zhou X, Wang F, Xie Y, et al. 2015). Therefore, it is desire in finding a novel *Lactobacillus* composition to replace antibiotics for the treatment of *Helicobacter pylori* infection.

SUMMARY OF THE INVENTION

In view of the above, the inventor is deeply aware of the deficiencies and defects of the existing technology, and is eager to improve and innovate. The inventor has successfully developed a *Lactobacillus* composition for inhibiting gastric *Helicobacter pylori*.

In order to achieve the above-mentioned object, the present invention provides a pharmaceutical composition for inhibiting gastritis induced by gastric *Helicobacter pylori*, comprising *Lactobacillus* selected from a group consisting of *Lactobacillus rhamnosus* GM-020 (also known as GMNL-74), with deposited number CCTCC M203098; *Lactobacillus acidophilus* GMNL-185, with deposited number CCTCC M2017764; and *Lactobacillus plantarum* GMNL-662, with deposited number CCTCC M2016571.

Wherein the pharmaceutical composition is a dosage form for oral administration, and the dosage form is selected from a group consisting of solution, suspension, emulsion, powder, pastille, pellet, syrup, troche, tablet, chewing gum, jatex and capsule.

In order to achieve the above-mentioned object, the present invention provides another food product, comprising *Lactobacillus rhamnosus* GM-020, *Lactobacillus acidophilus* GMNL-185, *Lactobacillus plantarum* GMNL-662 and an edible material.

Wherein the edible material is selected from a group consisting of water, fluid milk products, concentrated milk, yogurt, sour milk, frozen yogurt, lactic acid bacteria-fermented beverages, milk powder, ice cream, cream cheeses, hard cheeses, soy milk, fermented soy milk, vegetable-fruit juices, juices, sports drinks, confectionery, jelly, candies, infant foods, health foods, animal feeds, Chinese medicinal herbs compositions and dietary supplements.

In order to achieve the above-mentioned object, the present invention provides another method for treatment of a patient having gastric *Helicobacter pylori* infection, comprising administering to the patient a therapeutically effective amount of a *Lactobacillus* composition, wherein the *Lactobacillus* composition is selected from a group consisting of *Lactobacillus rhamnosus* GM-020, *Lactobacillus acidophilus* GMNL-185 and *Lactobacillus plantarum* GMNL-662.

Wherein the *Lactobacillus* composition achieve the efficacy of inhibiting multidrug-resistant gastric *Helicobacter pylori* and antibiotic-sensitive *Helicobacter pylori* by inhibiting the gastric *Helicobacter pylori* adhesion or invasion of gastric cells, inhibiting the gastric *Helicobacter pylori*-induced interleukine-8 (IL-8) and transcription factor NF-κB, and inhibiting the gastric COX-2 protein expression.

BRIEF DESCRIPTION OF THE DRAWINGS

FIG. 4A is a flowchart of mice fed with *Helicobacter pylori* and probiotics;

FIG. 4B is a chart of an analysis of degrees of *Helicobacter pylori* infection on gastric tissue by using CLO test; and FIG. 4C is an analysis of the expression of inflammatory protein COX-2 in gastric tissue by using immunohistochemical analysis method.

DETAILED DESCRIPTION OF THE INVENTION

All the technical and scientific terms mentioned in the specification are meanings that can be commonly understood by professionals of the field unless otherwise defined.

The terms "carrier," "vehicle," and "thinner" in this specification refer to non-toxic compounds or agents that have the function of assisting cells or tissues to absorb drugs.

A composition used in the present invention can be further added with an edible material for preparing as a food product or health care product. Wherein the edible material comprises but is not limited to: water; fluid milk products; milk; concentrated milk; fermented milk, such as yogurt, sour milk, frozen yogurt, lactic acid bacteria-fermented beverages; milk powder; ice cream; cream cheeses; hard cheeses; soy milk; fermented soy milk; vegetable-fruit juices; juices; sports drinks; confectionery; jelly; candies; infant foods; health foods; animal feeds; Chinese medicinal herbs; and dietary supplements.

The above-mentioned composition used in the present invention can be dietary supplements, which can be administrated in the following ways for a person who takes it: mixed with an appropriate potable fluid, such as water, yogurt, milk or juice; or mixed with solid or fluid foods. In the specification, the forms of dietary supplements can be pastille, pellet, capsule, lozenge, granule, powder, suspending agent, sachet, soft pastille, candy, syrup and corresponding administration forms; usually in the form of unit dose and is manufactured by conventional methods for preparing dietary supplements.

The *Lactobacillus* composition used in the present invention is a culture solution of dead bacteria or live bacteria.

The following embodiments are merely for exemplifications. Doses can be changed according to variations, and are not limited to the activity of chemical compounds being used, diseases being treated or physiological conditions, ways of administration, individual needs and requirements, severity of diseases and judgments of doctors.

Embodiment 1

Screening *Lactobacillus* composition that can be highly adhered to human gastric cells (AGS).

After human gastric epithelial cells AGS (ATCC CRL 1739) and activated *Lactobacillus* solution (multiplicity of infection MOI 100) are co-cultivated for 2 hours, the non-adhered bacteria are washed out with PBS and the cells are stained with Giemsa stain. The number of *Lactobacillus* adhered on the human gastric epithelial cells (AGS) is observed by using a microscope to evaluate the adhesion strength of the strains.

Figure 1:
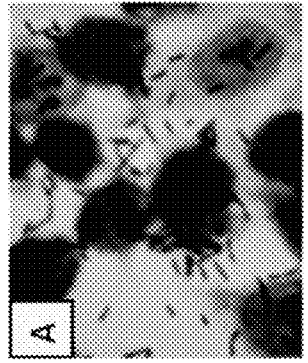
FIG. 1 is an organized diagram showing the ability of 226 *Lactobacillus* strains adhering to human gastric epithelial cells (AGS)
Figure 1:
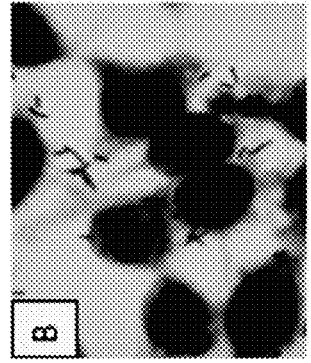
Figure 1:
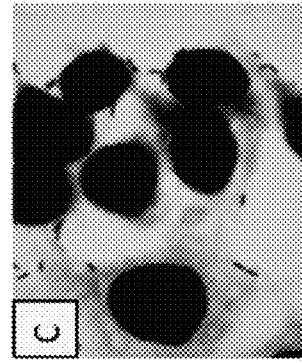
Figure 1:
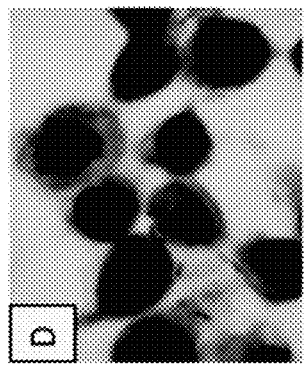
Figure 1:
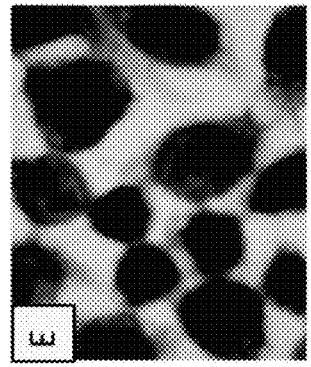

FIG. 1 shows the observation under the field of view of an oil immersion lens that if more than 40 *Lactobacillus* strains are adhered on the cells (as shown in FIG. 1 diagram A), they are expressed by "++++", indicating the ability to bind to the cells is the strongest; if more than 20 *Lactobacillus* strains are adhered on the cells (as shown in FIG. 1 diagram B), they are expressed by "+++"; if more than 10 *Lactobacillus* strains are adhered on the cells (as shown in FIG. 1 diagram C), they are expressed by "++"; if more than 3 *Lactobacillus* strains are adhered on the cells (as shown in FIG. 1 diagram D), they are expressed by "+"; and if no *Lactobacillus* strain is adhered on the cells (as shown in FIG. 1 diagram E), it is expressed by "−", indicating no binding ability to the cells.

Finally, the ability of a total of 226 *Lactobacillus* strains to bind to human gastric epithelial cells (AGS) is analyzed. 18 *Lactobacillus* strains with the highest binding ability are selected (FIG. 1 diagram F, marked "++++"), and their resistance to gastric acid are compared. Finally, 13 *Lactobacillus* strains that are more resistant to gastric acid are selected, and further screening for strains that are resistant to gastric *Helicobacter pylori* is conducted.

Embodiment 2

Screening of *Lactobacillus* strains that can highly inhibit IL-8 secretion and transcription factor NF-κB associated inflammatory response induced by *Helicobacter pylori*.

Gastric epithelial cells infected with *Helicobacter pylori* are cultivated with *Lactobacillus* containing the different strains (13 strains selected in the previous step) for 16 hours, and the IL-8 expression is analyzed by using ELISA. After the NF-κB luciferase construct is transfected into the gastric epithelial cells, *Lactobacillus* strains and *Helicobacter pylori* are added for co-cultivation for 12 hours. Then, the NF-κB-luciferase activity is analyzed to determine the activity of inflammatory response induced by *Helicobacter pylori*, and further analyzing whether the *Lactobacillus* strains have inhibitory effect.

The results of the analysis are shown in table 1. It can be known from the table that, the three strains of *Lactobacillus rhamnosus* GM-020 (also known as GMNL-74, presented in table as GMNL-74), *Lactobacillus acidophilus* GMNL-185 and *Lactobacillus plantarum* GMNL-662 have better ability to inhibit the secretion of IL-8, and inhibit the production of NF-κB, and the inhibitory effect is superior to the *Lactobacillus* of different strains of the same bacterium type.

TABLE 1

Screening results of *Lactobacillus* strains for inhibiting *Helicobacter pylori* - Induced inflammation associated factors

| No. | Strain | Concentration IL-8 (pg/mL, Mean ± SD) | NF-κB Activity (RLU, Mean ± SD) |
| --- | --- | --- | --- |
| 1 | Mock | 63.8 ± 3.0 | 123.54 ± 35.8 |
| 2 | HP alone | 7222.95 ± 275.2 | 31059.67 ± 16570.4 |
| 3 | L. acidophilus-GMNL-185 | 761.00 ± 10.2 | 232.84 ± 10.4 |
| 4 | L. acidophilus-G9 | 1034.75 ± 35.0 | 10214.87 ± 1145.3 |
| 5 | L. paracasei-H6 | 3578.89 ± 49.5 | 21892.95 ± 1245.6 |

TABLE 1-continued

Screening results of Lactobacillus strains for inhibiting Helicobacter pylori - Induced inflammation associated factors

| No. | Strain | Concentration IL-8 (pg/mL, Mean ± SD) | NF-κB Activity (RLU, Mean ± SD) |
|---|---|---|---|
| 6 | L. paracasei-H20 | 2314.34 ± 32.5 | 10123 ± 1150.3 |
| 7 | L. paracasei-H24 | 1267.54 ± 24.0 | 9123 ± 550.8 |
| 8 | L. paracasei-H25 | 1358.41 ± 26.5 | 10324.13 ± 1856.2 |
| 9 | L. rhamnosus-I7 | 4378.35 ± 56.5 | 11635.57 ± 2351.7 |
| 10 | L. rhamnosus-GMNL-74 | 148.22 ± 9.9 | 107.9182 ± 5.6 |
| 11 | L. rhamnosus-I44 | 2341.01 ± 46.5 | 10953.53 ± 1742.1 |
| 12 | L. plantarum-J13 | 1290.52 ± 33.9 | 10237.12 ± 1821.9 |
| 13 | L. plantarum-J20 | 1369.27 ± 28.5 | 10872.32 ± 1324.1 |
| 14 | L. plantarum-GMNL-662 | 234.06 ± 9.1 | 146.36 ± 25.7 |
| 15 | L. plantarum-J25 | 1461.06 ± 24.5 | 12537.67 ± 1235.3 |

The deposited number, date of deposit, and strain name of the three strains of Lactobacillus selected from the above table are shown in table 2.

TABLE 2

The deposited numbers of the Lactobacillus of the present invention in China

| Strain name | | Deposited number | Deposited date |
|---|---|---|---|
| Lactobacillus rhamnosus | GM020 (also known as GMNL-74) | CCTCC M203098 | Dec. 18, 2003 |
| Lactobacillus acidophilus | GMNL-185 | CCTCC M2017764 | Nov. 3, 2017 |
| Lactobacillus plantarum | GMNL-662 | CCTCC M2016571 | Oct. 17, 2016 |

Figure 2A:
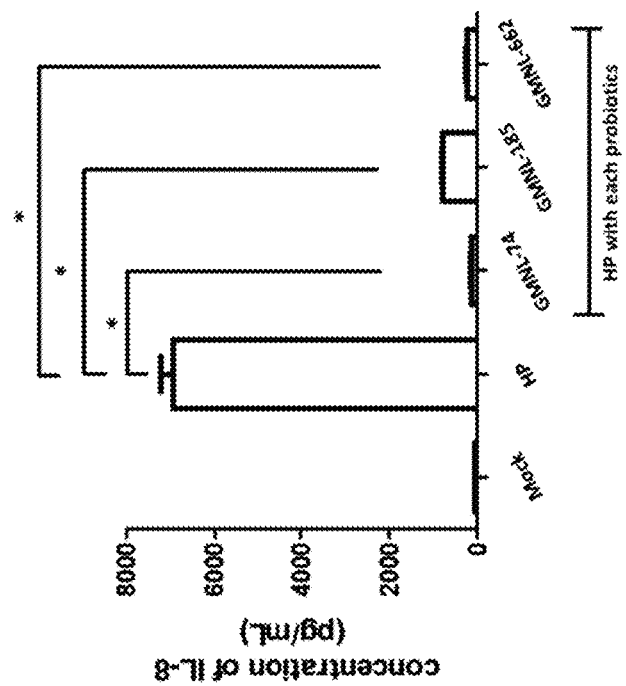
FIG. 2A is a chart of an analysis of IL-8 expression by using ELISA.
Figure 2B:
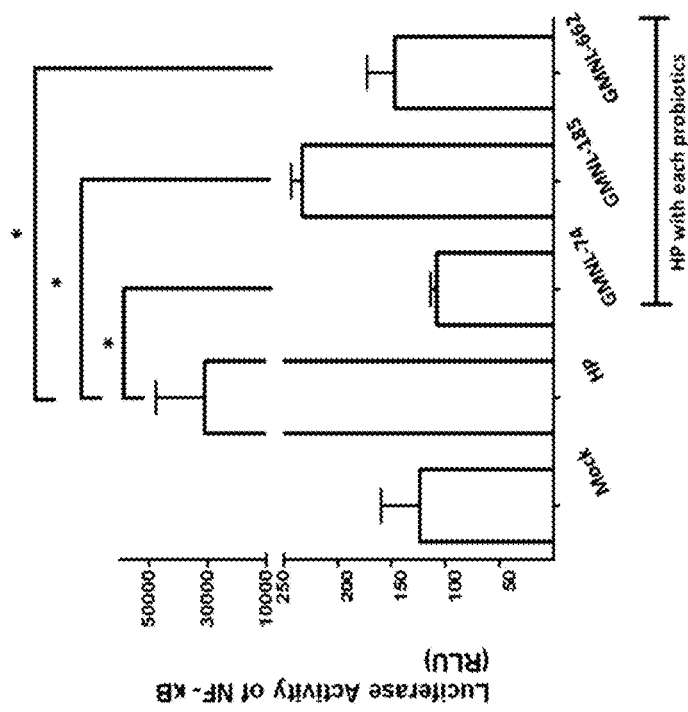
FIG. 2B is a chart of an analysis of NF-κB activity by using NF-κB luciferase analysis.

The gastric epithelial cells infected with Helicobacter pylori are co-cultivated with Lactobacillus containing different strains (13 strains selected in the previous step) for 16 hours, and the IL-8 expression is analyzed by using ELISA. The results are shown in FIG. 2 indicating the three strains selected from the table 1 having the best inhibition of Helicobacter pylori, wherein the comparison between the three strains and the experimental group (HP) is statistically significant (*: P<0.01). FIG. 2A shows the IL-8 expression and statistical analysis is conducted. It can be known from the figure that the three strains can inhibit the immuno-chemokine IL-8. FIG. 2B shows the relative activity of the transcription factor NF-κB and statistical analysis is conducted. It can be known from the figure that the three strains can inhibit the production of the transcription factor NF-κB of inflammatory response pathway. It can be known from the above conclusions that, the three strains show slightly different inhibition strengths, indicating that these three strains can reduce the infiltration of immune cells into the stomach and the severity of the promoted local inflammatory response by inhibiting the immuno-chemokine IL-8 and the production of the transcription factor NF-κB of inflammatory response pathway.

Embodiment 3

The three screened Lactobacillus strains have the activity of inhibiting both the adhesion and invasion of gastric epithelial cells by Helicobacter pylori.

In order to further confirm whether the Lactobacillus strains have the ability of inhibiting the adhesion activity of Helicobacter pylori on gastric epithelial cells, under the condition of containing the Lactobacillus strains, Helicobacter pylori infects the human gastric epithelial cells (AGS cells, ATCC CRL1739) with a multiplicity of infection (MOI) 100 for 6 hours. After washing the cells, the cells are disrupted with water, serially diluted and then inoculated into a blood culture medium. After cultivating for 3-4 days, the colony-forming units (CFUs) are counted, and the lower the CFU value indicates the number of Helicobacter pylori adhered on the cells is inhibited by the Lactobacillus.

The gentamicin protection assay is used to analyze the ability of Lactobacillus composition to influence the invasion activity of Helicobacter pylori in gastric epithelial cells. If the CFU decreases, it represents that the Lactobacillus composition has the effect of influencing the invasion activity of Helicobacter pylori in the gastric epithelial cells. The infected cells are washed with PBS three times and incubated with cell impermeable gentamicin (100 μg/ml) for 1.5 hours to kill the Helicobacter pylori on the surfaces. After washing, the cells are disrupted with water, serially diluted and then inoculated into a blood culture medium. After cultivating for 3-4 days, the colony-forming units (CFUs) of Helicobacter pylori are counted.

Figure 3B:
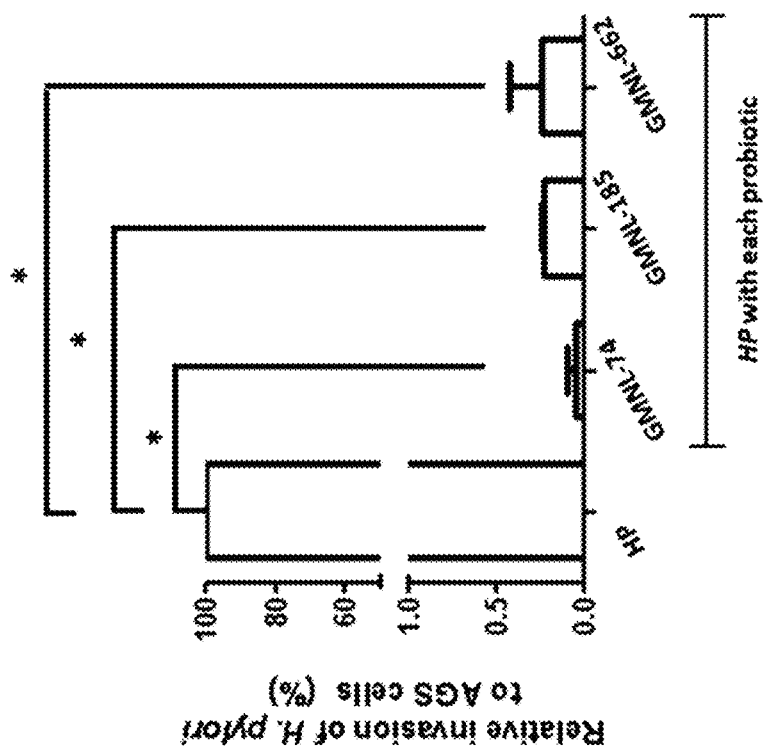
FIG. 3B is a chart of an analysis of *Lactobacillus* composition inhibiting the invasion of *Helicobacter pylori* into gastric epithelial cells.
Figure 3A:
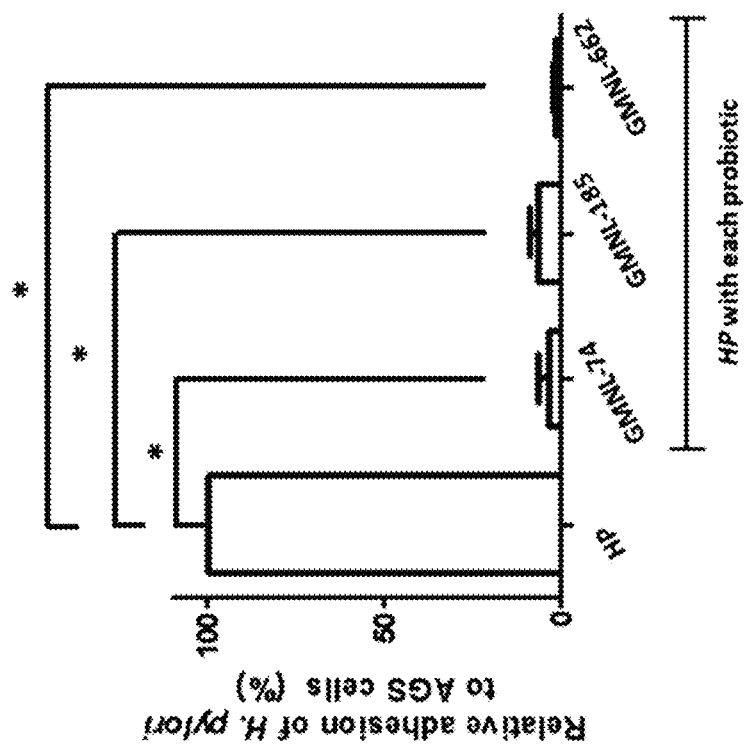
FIG. 3A is a chart of an analysis of *Lactobacillus* composition inhibiting the adhesion of *Helicobacter pylori* on gastric epithelial cells.

FIG. 3A is an analysis of the adhesion activity of Helicobacter pylori on gastric epithelial cells; and FIG. 3B is an analysis of the invasion activity of Helicobacter pylori in gastric epithelial cells. Wherein the ability of Helicobacter pylori to adhere on and invade into the gastric epithelial cells is simply considered as 100%, and statistical analysis is performed. After the analysis is compared, the comparison between the three strains and the experimental group (HP) is statistically significant (*: P<0.01).

The results show that these three strains of Lactobacillus can effectively reduce the adhesion of Helicobacter pylori on the gastric epithelial cells. The degree of inhibition can be up to more than 90% (as shown in FIG. 3A), and they are also more effectively in reducing the invasion of Helicobacter pylori into the gastric epithelial cells, the degree of inhibition is increased to above 99% (as shown in FIG. 3B). This provides that these three strains have good effect on inhibiting the adhesion and invasion of Helicobacter pylori in the gastric epithelial cells. In addition, under the two analysis platforms, the three strains have slightly different inhibition strengths. Therefore, the use of complex strains should be a preferred strategy.

Embodiment 4

A composition of the three strains of Lactobacillus has the effect of additive inhibition of antibiotic-sensitive Helicobacter pylori or multidrug-resistant Helicobacter pylori strains.

The agar-well diffusion method and bacteriostasis test are used to analyze the ability of the Lactobacillus strains resisting against the Helicobacter pylori strains. The H. pylori disease strains used include: H. pylori BCRC 26695 (ATCC 700392): wild-type strain with sensitivity to antibiotics metronidazole and clarithromycin; H. pylori v633: having resistance ($MZ^R$) to antibiotic metronidazole and resistance ($CH^R$) to antibiotic clarithromycin; and H. pylori v2311: having resistance ($MZ^R$) to antibiotic metronidazole but having sensitivity ($CH^S$) to antibiotic clarithromycin. The *H. pylori* are cultivated in microaerobic conditions (85% $N_2$, 10% $CO_2$, 5% $O_2$) and *Brucella* blood agar plate (BAP) culture medium. The pathogen are scraped off and the concentration of pathogen is adjusted to $1 \times 10^9$ cells/ml with PBS, take 100 μl of the diluted H. *pylori* and uniformly spread on a quantitative BAP culture plate, and allow to stand for 15 minutes until the surface of the culture medium is dry. Then, use a 11 mm diameter glass tube to dig hole in the above BAP culture medium that has been spread with the bacterial solution.

In order to confirm whether the bacteriostasis of the *Lactobacillus* is derived from the surface substances of the bacteria or from the secretory substances of the bacteria, the effect of bacteriostasis of the whole bacterial solution and the supernatant fluid with the bacteria eliminated are compared. The whole bacterial solution is collected in the following manner: after GM-020, GMNL-185 and GMNL-662 are activated overnight, they are cultivated to a MRS broth culture medium with 1% of inoculation amount, and the whole bacterial solution is collected after 18 hours of cultivation. At the same time, a mixed whole bacterial solution is prepared (ratio of the three *Lactobacillus* strains=1:1:1). The bacteria-eliminated supernatant fluid is collected in the following manner: after GM-020, GMNL-185 and GMNL-662 are activated overnight, they are cultivated to a MRS broth culture medium with 1% of inoculation amount, and the whole bacterial solution is collected after 18 hours of cultivation. After centrifugation at 13000 rpm for 3 minutes, the bacteria are removed, and the supernatant fluid is filtered with a 0.45 μm filter membrane to obtain the supernatant fluid. At the same time, a mixed supernatant fluid is prepared (ratio of the three *Lactobacillus* strains=1:1:1).

Finally, in the bacteriostasis test, first add 100 μl of the test sample of *Lactobacillus* strains in the hole, carefully move the culture plate horizontally to cultivate in microaerobic conditions and at 37° C. Then, observe the size of the inhibitory rings after 48 hours, and use an electronic vernier to measure the size inside the inhibitory rings. And conduct statistical analysis by using Student's t-test. *, P<0.05 indicates a significant difference to confirm whether the effect of mixed strains is better than that of single strain.

The results shows that, whether the gastric *Helicobacter pylori* strains are HP wild type, which has antibiotic sensitivity, or single drug or multidrug-resistant (HP v2311: $MZ^R$; HP v633: $MZ^R$, $CH^R$), both the whole bacterial solution and the bacteria-eliminated supernatant fluid of GM-020 (also known as GMNL-74, presented in table as GMNL-74), GMNL-185 and GMNL-662 have obvious bacteriostasis ability, but the ability to inhibit each pathogen is different (as shown in table 3 and table 4). The bacteriostasis ability of the whole bacterial solution is better than that of the supernatant fluid, indicating that both the surface substances of the bacteria and the secretory substances of the bacteria have the ability to inhibit the gastric *Helicobacter pylori*. More particularly, the bacteriostasis ability of the GM-020, GMNL-185 and GMNL-662 *Lactobacillus* composition is significantly stronger (P<0.05) than that of a single strain, indicating that the use of this *Lactobacillus* composition can enhance the anti-*Helicobacter pylori* effect. And at the same time, the composition also has excellent inhibitory effect for a plurality of clinically drug-resistant strains simultaneously, and is not subject to the limitations encountered when clinically treating with antibiotics.

TABLE 3

Results of inhibitory rings of inhibiting *Helicobacter pylori* by whole bacterial solution of *Lactobacillus* strains

|  | HP wild type | P value | HP v2311 | P value | HP v633 | P value |
|---|---|---|---|---|---|---|
| GMNL-74 | 14.4 ± 0.1 | 0.076 | 8.8 ± 0.0 | 0.000 | 10.5 ± 0.8 | 0.003 |
| GMNL-185 | 10.6 ± 0.1 | 0.009 | 8.6 ± 0.4 | 0.033 | 9.2 ± 0.2 | 0.003 |
| GMNL-662 | 14.0 ± 0.1 | 0.020 | 9.8 ± 0.2 | 0.019 | 1.31 ± 0.8 | 0.024 |
| *Lactobacillus* composition | 15.2 ± 0.0 |  | 13.8 ± 0.0 |  | 16.3 ± 1.7 |  |

Note:
*Lactobacillus* composition = GM-020(GMNL-74) + GMNL-185 + GMNL-662

TABLE 4

Results of inhibitory rings of inhibiting *Helicobacter pylori* by supernatant fluid of *Lactobacillus* strains

|  | HP wild type | P value | HP v2311 | P value | HP v633 | P value |
|---|---|---|---|---|---|---|
| GMNL-74 | 6.2 ± 0.2 | 0.025 | 7.1 ± 0.2 | 0.014 | 6.5 ± 0.0 | 9E−08 |
| GMNL-185 | 5.7 ± 0.1 | 0.004 | 6.5 ± 0.0 | 0.001 | 5.9 ± 0.3 | 0.00047 |
| GMNL-662 | 5.3 ± 0.2 | 0.012 | 8.6 ± 0.2 | 0.032 | 6.8 ± 0.1 | 9.9E−05 |
| *Lactobacillus* composition | 7.6 ± 0.1 |  | 10.4 ± 0.1 |  | 7.8 ± 0.1 |  |

Note:
*Lactobacillus* composition = GM-020(GMNL-74) + GMNL-185 + GMNL-662

Embodiment 5

The combination of the three *Lactobacillus* strains can significantly reduce the degree of gastric tissue infection and reduce the gastric inflammatory response of *H. pylori*-infected mice.

The protective effect of the *Lactobacillus* composition is evaluated by analyzing the inflammatory response of mice using the *Helicobacter pylori* mouse test model experiment. Six-week-old BALB/c mice are divided into three groups: the first group is the control group (Mock), the second group is the experimental group (inoculated with *Helicobacter pylori*), and the third group is daily tube-fed *Lactobacillus* composition (GM-020+GMNL-185+GMNL-662). Each group of the experimental mice is daily pre-fed with water or *Lactobacillus* composition (Group 3). The amount of *Lactobacillus* is $2.4 \times 10^7$ CFU/time/mouse and continues until the 24th day. The experimental mice (the second and third groups) are inoculated with *Helicobacter pylori* on the afternoon of the 8th, 10th, 12th, 14th, 16th and 18th day (as shown in FIG. 4A) for a total of six times, and the amount of bacteria is $1 \times 10^9$ CFU/time/mouse. Inoculation of *Helicobacter pylori* is stopped on the eighteenth day of feeding, and feeding of *Lactobacillus* composition still continues.

On the 25th day, the mice are sacrificed, gastric tissues are taken and the *Helicobacter pylori* urease activity is analyzed by using the CLO (*Campylobacter*-like Organism) Test. If the CLO test culture medium shows red to pink, it means that the mouse stomach is still infected with *Helicobacter pylori*, which is a positive reaction; if it shows yellow, it indicates a negative reaction. The color depth is quantified and drawn as a histogram (as shown in FIG. 4B), and statistical analysis is performed to analyze whether the *Lactobacillus* composition can inhibit the *Helicobacter pylori* infection. The results of the CLO test are shown in FIG. 4B. The results show that the value of the gastric CLO scoring in the tube-fed mixed strains (GM-020+GMNL-185+GMNL-662) group is significantly lower than that of the group inoculated with *Helicobacter pylori* only, which is statistically significant compared with the experimental group (HP) (*: $P<0.05$).

The expression of the inflammatory factor cyclooxygenase-2 (COX-2) in gastric tissues is analyzed by immunohistochemical staining method and background H&E staining to evaluate the gastric inflammatory response when the *Lactobacillus* composition is inhibiting the *Helicobacter pylori* infection in order to infer the possible mechanisms.

The results in FIG. 4C show that feeding mixed strains can significantly inhibit the COX-2 protein expression.

In summary, the present invention screens 226 strains of *Lactobacillus* to find a *Lactobacillus* composition for anti-*Helicobacter pylori*, among them comprising: *Lactobacillus rhamnosus* GM-020, *Lactobacillus acidophilus* GMNL-185 and *Lactobacillus plantarum* GMNL-662. In addition to the *Lactobacillus* composition having the ability to bind to gastric epithelial cells, but also has the ability to reduce the immunochemotaxis and inflammatory response induced by the gastric *Helicobacter pylori* infection. In addition, the *Lactobacillus* composition can effectively inhibit the gastric *Helicobacter pylori* adhesion and invasion of gastric epithelial cells, and compared to a single strain, the *Lactobacillus* composition has an additive effect of inhibiting multiple *Helicobacter pylori* strains. It indicates that this *Lactobacillus* composition is very helpful for widely using in the treatment of clinically occurring antibiotic-resistant *Helicobacter pylori* strains.

In addition, both the whole bacterial solution and supernatant fluid have the effect of inhibiting the *Helicobacter pylori* strains, and the effect of the whole bacterial solution on inhibiting *Helicobacter pylori* is better than that of the supernatant fluid, indicating that both the surface substances of the bacteria and the secretory substances of the bacteria of GM-020, GMNL-185 and GMNL-662 have the ability to inhibit the gastric *Helicobacter pylori*. Furthermore, the *Lactobacillus* composition can reduce the secretion of the immuno-chemokine IL-8 caused by *Helicobacter pylori* and reduce the increase of the inflammation-associated transcription factor NF-κB, and can also reduce the increase of the inflammatory response of gastric COX-caused by *Helicobacter pylori*. The results indicate that the *Lactobacillus* composition of the present invention can be used to prevent or treat a large number of subsequent diseases caused by the gastric *Helicobacter pylori* infection, for examples, gastric ulcer, duodenal ulcer, chronic gastritis, gastric cancer, etc. Additionally, the *Lactobacillus* composition of the present invention has no side-effects and therefore it can be used as another excellent choice for the treatment of gastric *Helicobacter pylori* infection-associated diseases.

Note that the specification relating to the above embodiments should be construed as exemplary rather than as limitative of the present invention, with many variations and modifications being readily attainable by a person of average skill in the art without departing from the spirit or scope thereof as defined by the appended claims and their legal equivalents.

What is claimed is:

1. A method for inhibiting gastritis induced by gastric *Helicobacter pylori*, comprising administering a therapeutically effective amount of a *Lactobacillus* composition, wherein the *Lactobacillus* composition is selected from a group composed of *Lactobacillus rhamnosus* GM-020 (also known as GMNL-74), *Lactobacillus acidophilus* GMNL-185, and *Lactobacillus plantarum* GMNL-662;
   wherein the deposited numbers of the *Lactobacillus rhamnosus* GM-020 are BCRC910236 and CCTCC M203098, the deposited numbers of the *Lactobacillus acidophilus* GMNL-185 are BCRC910774 and CCTCC M2017764, and the deposited numbers of the *Lactobacillus plantarum* GMNL-662 are BCRC910738 and CCTCC M2016571.

2. The method as claimed in claim 1, wherein the therapeutically effective amount is $10^6 \sim 10^8$ CFU per time.

3. The method as claimed in claim 1, wherein the *Lactobacillus* composition achieve the efficacy of inhibiting gastritis induced by gastric *Helicobacter pylori* by inhibiting the gastric *Helicobacter pylori* adhesion or invasion of gastric epithelial cells.

4. The method as claimed in claim 1, wherein the *Lactobacillus* composition can further inhibit the gastric *Helicobacter pylori*-induced interleukine-8 (IL-8) and transcription factor NF-κB.

5. The method as claimed in claim 1, wherein the *Lactobacillus* composition can further inhibit the gastric COX-2 protein expression.

6. The method as claimed in claim 1, wherein the *Lactobacillus* composition comprise a culture solution of one of surface substances of the bacteria and secretory substances of the bacteria, or a combination of both.

7. The method as claimed in claim 1, wherein the *Lactobacillus* composition are dead bacteria or live bacteria.

8. The method as claimed in claim 1, wherein the gastric *Helicobacter pylori* are multidrug-resistant *Helicobacter pylori* strains or antibiotic-sensitive *Helicobacter pylori* strains.

* * * * *